United States Patent [19]
Palmer et al.

[11] Patent Number: 6,106,804
[45] Date of Patent: Aug. 22, 2000

[54] ARSENIC-72 LABELED COMPOUNDS FOR TISSUE SPECIFIC MEDICAL IMAGING

[75] Inventors: Robert B. Palmer; Jerry L. Born, both of Albuquerque, N. Mex.

[73] Assignee: The University of New Mexico, Albuquerque, N. Mex.

[21] Appl. No.: 08/874,946

[22] Filed: Jun. 13, 1997

[51] Int. Cl.$^7$ .......................... A61K 49/00; G01N 31/00; G01N 33/48

[52] U.S. Cl. .................. 424/9.1; 424/1.11; 424/1.65; 424/1.81; 424/1.69

[58] Field of Search .................... 424/1.11, 1.65, 424/1.81, 9.1, 1.69, 9.3, 9.4, 9.5, 9.6; 534/7, 10–16; 530/300, 326, 328, 327, 330

[56] References Cited

U.S. PATENT DOCUMENTS

| | | | |
|---|---|---|---|
| 5,169,933 | 12/1992 | Anderson et al. | |
| 5,443,816 | 8/1995 | Zamora et al. | 424/1.65 |
| 5,460,785 | 10/1995 | Rhodes et al. | 424/1.49 |

FOREIGN PATENT DOCUMENTS

| | | |
|---|---|---|
| 96/23527 | 8/1966 | WIPO . |
| 92/18536 | 10/1992 | WIPO . |
| 93/12819 | 7/1993 | WIPO . |
| 95/11694 | 5/1995 | WIPO . |

OTHER PUBLICATIONS

Hembrough, T.A; Li, L; Gonias, S.L; Cell–Surface Cytokeratin–8 is the Major Plasminogen Receptor on Breast Cancer cels and is Required for the Accelerated Activation of Cell–Associated Plasminogen by Tissue–Type Plasminogen Activator. J. Biol Chem (1996); 271(41):25684–25691.

Palmer, R.B; Upthagrove, A. L; Nelson, W.L;(E)– nd (Z)–7–Arylidenenaltrexones: Synthesis and Radioligand Displacement Assays. J Med Chem (1997); 40(5):749–753.

Fortunati, N; Fissore, F; Fazzari, A; Becchis, M; Comba, A; Catalano, M.G; Berta, L; Frairia, R; Sex–Steriod Binding Protein Exerts Negative Control on Estradiol Action in MCF–7 Cells (Human Breast Cancer) Through Cyclic Adenosin 3',5'–Monophosphate and Protein Kinase A. Endocrinology (1996); 137(2):686–692.

Williams, C.L; Stancel, G.M; Estrogens and Progestins. In, Goodman and Gilman's The Pharmacological Basis of Therapeutics, 9th Ed., J.G. Hardman and L.E. Limbird (Eds.), McGraw–Hill: New York, (1996); 1423–1440.

Banerjee, R; Ginsburg, E; Vonderhaar, B.K; Characterization of a Monoclonal Antibody Against Human Prolactin Receptors. Int J ancer (1993); 55(5):712–721.

Reubi, J.C; In Vitro Identification of Vasoactive Intestinal Receptors in Human Tumors: Implications for Tumor Imaging. J Nucl Med (1995); 36(10):1846–1853.

Fritta, L; Vigneri, R; Papa, V; Goldfine, I.D; Grasso, D; Trischitta, V; Structural and Functional Studies of Insulin Receptors in Human Breast Cancer Res Treat (1993); 25(1):73–82.

Formento, J.L; Francoual, M; Formento, P; Eitenne, M.C; Fischel, J; Namer, M; Frenay, M; Francois, E; Milano, G; Epidermal Growth Factor Receptor Assay: Validation of a Single Point Method and Application to Breast Cancer. Breast Cancer Res Treat (1991); 17(3):211–219.

N. Touchette, Breast Cancer: Roulette or Calculated Risk;, J. NIH Research, Oct., 33, (1993).

D.P. Swanson, J.M. Chilton and J.H. Thrall, Pharmaceuticals in Medical Imaging, MacMillan Publishing Company: New York, v–viii, (1990).

S. Jurrison, D. Berning, W. Jia and D. Ma, Chem. Rev., 93, 1137, (1993).

A.–C. Chang, C.C. Chaoo, A.E. Takemori, G. Gekker, S. Hu, P.K. Peterson and P.S. Portoghese, J. Med. Chem., 39, 1729, (1996).

J.B. Arterburn, I.M. Fogarty, K.A. Hall, K.C. Ott and J.C. Bryan, Functionalized Organoimidorhenium (V) Complexes as Potential Radiopharmaceuticals: Syntheses of Glycine Derivatives and the Structure Determination of a Rhenium Analogue of Chlorambucil. Angew. Chem. Int. Ed. Engl., 35, 2877, (1996).

A.J. Gordon and R.A. Ford, The Chemist's Companion: A Handbook of Practical Data, Techniques and References. John Wiley and Sons: New York, NY, 83, (1972).

E.P. Adams, F.P. Doyle, W.H. Hunter and J.H.C. Nayler, J. Chem. Soc., 2674, (1960).

P.J.E. Brownlee, M.E. Cox, B.O. Handford, J.C. Marsden and G.T. Young, Jr. Chem. Soc., 3832, (1964).

R.W. Bruggenmeier, D.D. Miller and D.T. Witiak, Cholesteol, Adrenocorticoids and Sex Hormones. In, Principles of Medicinal Chemistryl, 4th ed., W.O. Foye, T.L. Lemke and D.A. Williams (Eds.), Williams and Wilkins: Media, PA, 444–498, (1995).

*Primary Examiner*—Jose' G. Dees
*Assistant Examiner*—Dameron Jones
*Attorney, Agent, or Firm*—Hoffman, Wasson & Gitler, PC

[57] ABSTRACT

Radioactive arsenic ($^{72}$As) labelled tissue specific ligands are prepared and used in the medical imaging of malignant breast or prostate tumors.

11 Claims, No Drawings

ARSENIC-72 LABELED COMPOUNDS FOR TISSUE SPECIFIC MEDICAL IMAGING

BACKGROUND OF THE INVENTION

The invention is directed to the use and preparation of radioactive arsenic ($^{72}$As) labelled tissue-specific ligands useful in the medical imaging of breast cancer.

Breast cancer is of tremendous societal concern. According to the United States National Cancer Institute, approximately 182,000 new cases of breast cancer will be diagnosed each year; furthermore, the American Cancer Society estimates that 1 out of every 9 women will develop breast cancer at some point during their lives. Therefore, early detection and diagnosis of the disease as well as tracking of existing tumors is of great interest. Diagnostic medical imaging is a tool used for these purposes. In some cases, radioactive isotopes are employed as diagnostic aids. However, a lack of tumor tissue selectivity in the delivery of the radioisotope does not optimize their diagnostic utility.

Therefore, selection of an appropriate delivery ligand is paramount. The delivery of the radioisotope to the desired tissue or site of action is based on the recognition and binding of a small molecule or peptide by a receptor unique to that tissue. If a ligand with a preference for binding to malignant breast tissue is known, conjugation of this ligand to a radioisotope will be of great potential clinical utility. Not only will it be possible to monitor progression of old tumors and discover new ones, but previously undetectable metastases may become visible.

Contemporary medical imaging depends largely upon the use of radioisotopes. One of the first clinically employed metals of this type is technetium (Tc). This element was first administered to a human subject in the form of Na$^{99m}$TcO$_4$ in 1961. Despite the rapid progress in development of $^{99}$Tc as a diagnostic aid, organ and cell-specific delivery of the radioactive ligand remains one of the largest challenges in the field. Other radioisotopes including halogens such as $^{125}$I, $^{131}$I and $^{82}$Br and isotopes of various metals including lead, gallium, rhenium, arsenic and copper have also been explored as potential imaging agents. However, simply changing the radioisotope does little to alter site-specific delivery.

A previously successful approach to site-specific receptor probe delivery is through the conjugation of an active agent with an affinity for a specific receptor contained within the tissue of interest to a probe with no inherent biological activity. Attempts have been reported using this methodology for the delivery of radioisotopes to specific areas for medical imaging purposes. One such report is described in WO 92/18536 wherein various radioactive isotopes were attached directly to derivatives and fragments of the peptide pituitary adenylate cyclase-activating polypeptide (PACAP). However, as is stated within that very document, "the great number of different mammalian tissues having PACAP receptors will make selective use of this peptide in medicine very difficult." A slightly more successful agent is an $^{111}$In labeled cyclic octapeptide marketed under the name "OctreoScan" with a purported specificity for abdominal tumors.

Despite publications filed on labeled compounds for medical imaging, much work still remains unfinished. The most difficult part of this process is the selection of an appropriate peptide or small molecule and the subsequent derivitization of this compound in such a manner as to not detrimentally affect its recognition by or binding to its receptor.

It is an object of the present invention to provide a methodology for the preparation of $^{72}$As labelled biologically active molecules and their incorporation into peptides and/or small receptor targeted molecules to provide new imaging and therapeutic agents.

It is a further object of the invention to use the inventive ligands as medical imaging agents.

SUMMARY OF THE INVENTION

The invention describes the synthesis of a series of compounds that have a high affinity for a particular anatomical region or tumor type that are amenable to attachment to a radioactive metal ($^{72}$As) useful in medical imaging. Specifically, biologically active molecules with a known affinity for receptors present within malignant breast or prostate tumors are provided.

Provided are organoarsenic imaging agents as described by the following general structure:

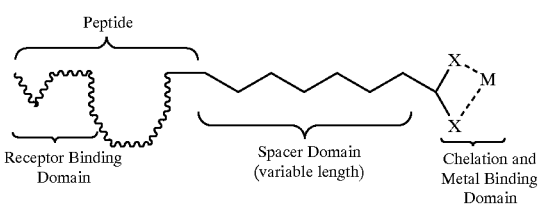

The compounds are composed of three main parts: a receptor binding/recognition domain; a spacer domain and a chelating ligand through which the radioisotope will be attached.

DETAILED DESCRIPTION OF THE INVENTION

The organoarsenic imaging agents of the present invention are composed of three main parts.

The receptor binding/recognition domain of the compounds will be either a peptide or a small organic molecule. In either case, the molecule possesses known receptor specificity. In other words, the peptide or small molecule has a documented affinity and favorable binding kinetics at a receptor site in a tissue of interest. Regarding breast cancer, the drugs tamoxifen and diethylstilbesterol (DES) both fit these requirements. This portion of the imaging compounds will be used as the delivery agent as well as the receptor recognition and binding domain.

The introduction of the spacer domain to the prepared agents is also of high importance to binding. The binding characteristics of the receptor recognition and binding domain are dependent upon the size and geometry as well as hydrophilicity of the molecule. If the geometry of the ligand is distorted or its dimensions within the binding confines of the receptor made too large, the ligand-receptor complex will not form and no tissue specificity will be imparted. Since arsenic has an average single bond colvalent atomic radius of 121 pm (roughly 1.6 times larger than carbon), it is necessary to make sure this atom is well removed from potentially devastating interactions with receptor. The function of the spacer domain is to tether the arsenic to the receptor recognition ligand while not allowing the large atomic size of the metal to prevent binding to the receptor. This allows specific delivery of the radioactive arsenic to the tissue receptor of interest for imaging.

For suitable peptide ligands, the peptide will be coupled to the spacer and the spacer to a lipoic acid appendage using dicyclohexylcarbodiimide (DCC) chemistry. This technique is the standard for peptide preparation and derivatization within the chemical industry. Next, the reduction of the disulfide bond in the lipoic acid to the dithiol will be accomplished. Mild conditions must be used so as to not affect any other portion of the peptide. Though numerous mild techniques for this type of reduction exist, preferred is the removal of a S,S'-isopropylidene protecting group with mercury(II)chloride and aqueous mercury(II)acetate cleavage of a protected S-phenylthiomethyl dithioacetal. Once the dithiol is formed, addition of $As^{+3}$ will result in formation of a covalently bound arsenic through two sulfur-arsenic bonds (see below). This will be done first using "cold" (a non-radioactive isotope) arsenic and then, following satisfactory results, $^{72}As$ will be incorporated.

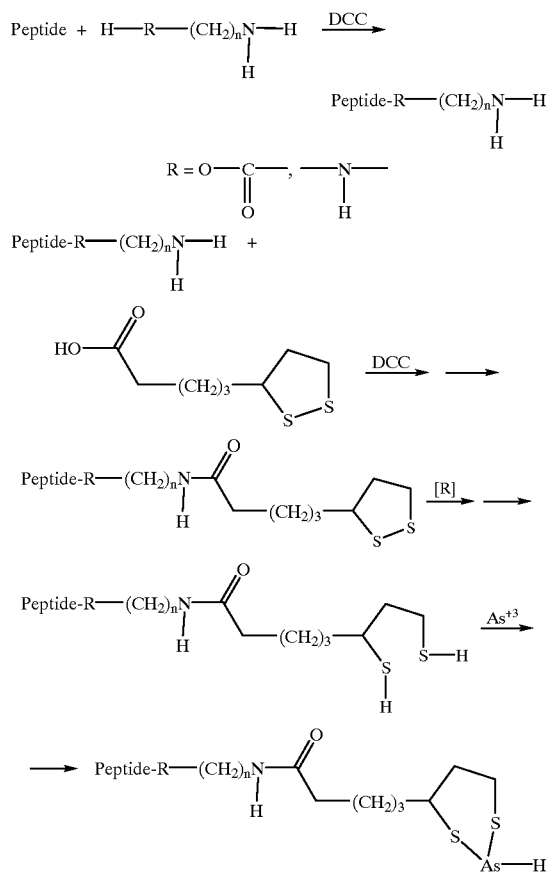

The detection, purification and characterization of the prepared compounds will involve standard reverse-phase high performance liquid chromatography (HPLC). Ultraviolet as well as radiochemical detection methods will be employed. Following purification, the compound(s) will be ready for binding and specificity assessment.

The modification of either steroids or steroid surrogates provides an opportunity to identify cellular populations with high densities of a receptor. The estrogen receptor is implicated in breast cancer and the use of antiestrogens in the treatment of estrogen dependent tumors is recognized as important therapeutically. This strategy is less attractive than modification of peptides due to the relatively large change in the physical characteristics of the compound with the incorporation of a functional group capable of chelation of arsenic. Specifically ethers of estrogens, which contain a lipoic acid-like group, are prepared for the chelation of arsenic as shown in the figure below.

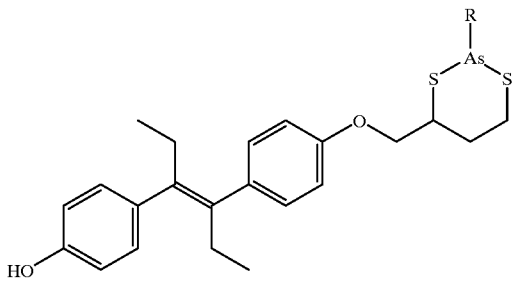

From the foregoing, it will be appreciated that, although specific embodiments of the invention have been described herein for the purposes of illustration, various modifications may be made without deviating from the spirit and scope of the invention. Accordingly, the invention is not limited by the appended claims.

What is claimed:

1. A medical imaging composition for targeting in vivo tissues having ligand receptors therein, comprising:
   a. a receptor binding domain compound selected from tamoxifen or diethylstilbestrol with known receptor specificity;
   b. a spacer domain agent coupled to said receptor binding domain compound; and
   c. a radioactive arsenic coupled to said spacer domain.

2. A medical imaging composition in accordance with claim 1, wherein said receptor binding domain compound is a peptide or a small organic molecule with an affinity for said in vivo tissue.

3. A medical imaging composition in accordance with claim 1; wherein said radioactive arsenic is $^{72}As$.

4. A medical imaging composition in accordance with claim 1 as follows:

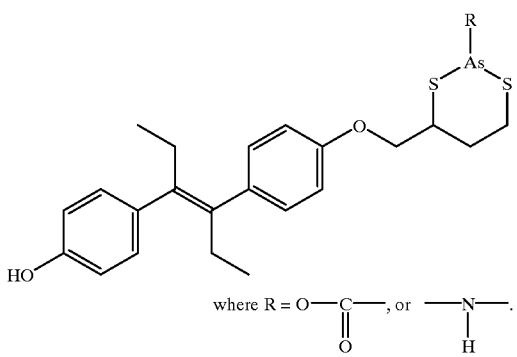

5. A method of imaging a tissue in vivo, said tissue having ligand receptors therein;
   said method comprising the steps
      applying a labelled medical imaging composition as claimed in claim 1 to said tissue;
      allowing a portion of said labelled ligand material to join with said ligand receptors in said tissue, and
      thereafter obtaining an image of said labelled ligand marked in said tissue by utilization of a detection means positioned to detect radiation from said radioactive component.

6. A medical imaging composition for targeting in vivo tissues having ligand receptors therein, comprising:

a. a receptor binding domain compound with known receptor specificity;
b. a spacer domain agent coupled to said receptor binding domain compound; and
c. a radioactive arsenic coupled to said spacer domain wherein the medical imaging composition is:

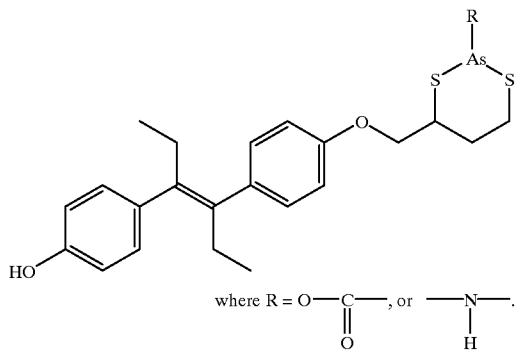

where R = O—C(=O)—, or —N(H)—.

7. A medical imaging composition in accordance with claim 6, wherein said receptor binding domain compound is a peptide or a small organic molecule with an affinity for said in vivo tissue.

8. A medical imaging composition in accordance with claim 6, wherein said receptor binding domain compound is tamoxifen or diethylstilbestrol.

9. A medical imaging composition in accordance with claim 6, wherein said radioactive arsenic is $^{72}$As.

10. A process of producing a medical imaging composition as claimed in claim 6, comprising the steps of
   i) coupling a peptide receptor binding domain compound to said spacer domain agent in the presence of dicyclohexyl carbodiimide (DCC) to form an intermediate;

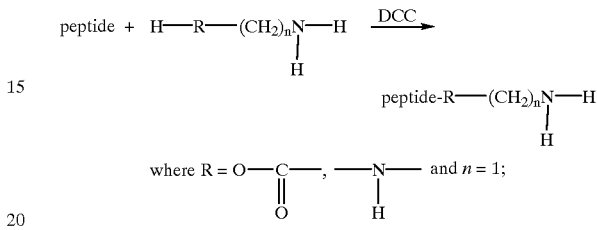

where R = O—C(=O)—, —N(H)— and $n = 1$;

ii) coupling said intermediate to a lipoic acid in the presence of said peptide and said spacer compound and then reducing a resultant disulfide to a dithiol as follows:

ii) coupling said intermediate to a lipoic acid in the presence of said peptide and said spacer compound and then reducing a resultant disulfide to a dithiol as follows:

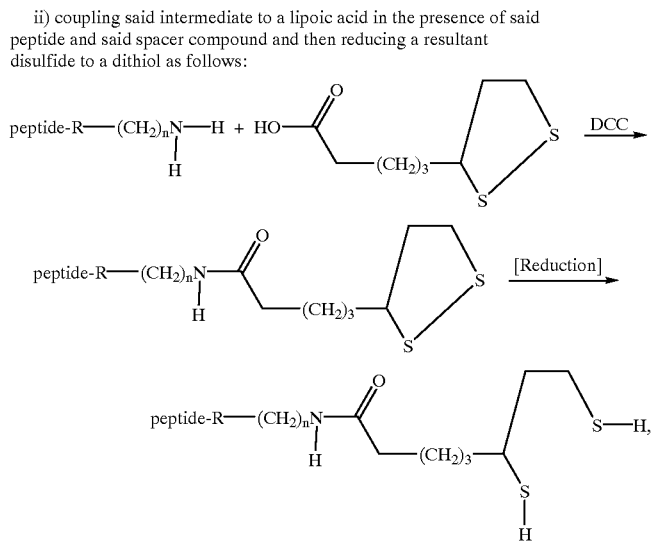

to form said dithiol intermediate:

iii) coupling said radioactive aresenic to said dithiol intermediate as follows:

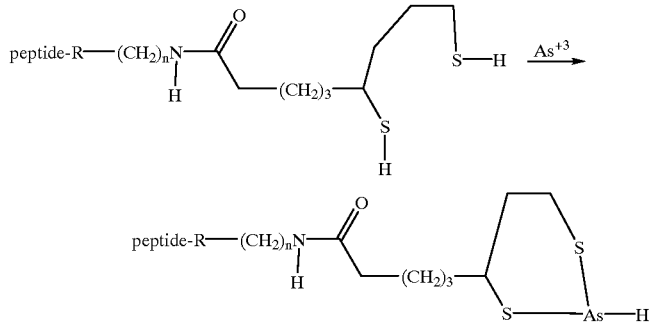

to form said medical imaging composition.

11. A method of imaging a tissue in vivo, said tissue having ligand receptors therein;

said method comprising the steps
applying a labelled medical imaging composition as claimed in claim 6 to said tissue;
allowing a portion of said labelled ligand material to join with said ligand receptors in said tissue; and
thereafter obtaining an image of said labelled ligand marked in said tissue by utilization of a detection means positioned to detect radiation form said radioactive component.

\* \* \* \* \*